(12) United States Patent
Bell et al.

(10) Patent No.: US 11,612,451 B2
(45) Date of Patent: Mar. 28, 2023

(54) DENTAL SCANNING METHODS FOR ANALYZING JAWS

(71) Applicants: Patrick C. Bell, La Crosse, WI (US); Leo J. Malin, La Crosse, WI (US); Thomas J. Arendt, Norwalk, WI (US)

(72) Inventors: Patrick C. Bell, La Crosse, WI (US); Leo J. Malin, La Crosse, WI (US); Thomas J. Arendt, Norwalk, WI (US)

(*) Notice: Subject to any disclaimer, the term of this patent is extended or adjusted under 35 U.S.C. 154(b) by 596 days.

(21) Appl. No.: 16/783,678

(22) Filed: Feb. 6, 2020

(65) Prior Publication Data
US 2021/0244515 A1 Aug. 12, 2021

(51) Int. Cl.
*A61C 9/00* (2006.01)
*G06V 10/22* (2022.01)
(Continued)

(52) U.S. Cl.
CPC ............ *A61B 90/39* (2016.02); *A61C 9/0046* (2013.01); *A61C 13/0004* (2013.01);
(Continued)

(58) Field of Classification Search
CPC ... A61C 9/0046; A61C 13/0004; A61C 9/004; A61C 19/05; A61C 13/00; A61B 90/39; A61B 2090/3912; A61B 2090/3916; A61B 2090/3991; A61B 5/055; A61B 6/032; A61B 6/14; A61B 6/4085; A61B 90/00; A61B 2090/3904; A61B 6/03; A61B 6/02; G06V 20/20; G06V 10/22;
(Continued)

(56) References Cited

U.S. PATENT DOCUMENTS

| | | |
|---|---|---|
| 5,415,546 A | 5/1995 | Cox, Sr. |
| 6,073,044 A | 6/2000 | Fitzpatrick et al. |

(Continued)

FOREIGN PATENT DOCUMENTS

| | | |
|---|---|---|
| EP | 1599148 B1 | 4/2011 |
| KR | 101594497 B1 | 2/2016 |

(Continued)

OTHER PUBLICATIONS

Tab2, Summary of Safety and Effectiveness, 510(k) Summary per 21 CFR 807.92(c), Self-Drilling Radiographic Marker, Jacksonville, Florida, 4 pages, published May 13, 2004.
(Continued)

*Primary Examiner* — Ralph A Lewis
*Assistant Examiner* — Mirayda A Aponte
(74) *Attorney, Agent, or Firm* — bobharter.com; Robert J. Harter

(57) ABSTRACT

Example dental scanning methods for analyzing jaws of a patient involve taking multiple scans of the jaws, and/or models thereof, and then shifting the image of one scan to match that of another. In some examples, fiducial markers are attached to the patient's jaws beforehand to accurately identify and track the relative position of the jaws. The methods provide a way for creating a precise image of an upper jaw and a lower jaw in their proper bite registration, even though the resulting image may show an insufficient number of teeth to readily do so. The final, properly shifted image serves as a virtual 3D jaw model that can be manipulated and analyzed to aid in various orthodontic and other dental treatments.

16 Claims, 13 Drawing Sheets

(51) Int. Cl.
| | |
|---|---|
| *G06V 20/20* | (2022.01) |
| *A61B 5/055* | (2006.01) |
| *A61B 6/03* | (2006.01) |
| *A61B 6/00* | (2006.01) |
| *A61B 6/14* | (2006.01) |
| *A61B 90/00* | (2016.01) |
| *A61C 13/00* | (2006.01) |

(52) U.S. Cl.
CPC .............. *G06V 10/22* (2022.01); *G06V 20/20* (2022.01); *A61B 5/055* (2013.01); *A61B 6/032* (2013.01); *A61B 6/14* (2013.01); *A61B 6/4085* (2013.01); *A61B 2090/3912* (2016.02); *A61B 2090/3916* (2016.02); *A61B 2090/3991* (2016.02); *G06V 2201/033* (2022.01)

(58) Field of Classification Search
CPC ......... G06V 2201/033; G06V 2201/03; G06V 2201/00; G06T 2207/00
USPC ........ 433/29; 382/154, 128; 250/234, 227.2, 250/370, 2, 363.2; 356/601, 608; 359/17
See application file for complete search history.

(56) References Cited

U.S. PATENT DOCUMENTS

| | | | |
|---|---|---|---|
| 6,096,048 | A | 8/2000 | Howard, III et al. |
| 6,102,914 | A | 8/2000 | Bulstra et al. |
| 6,333,971 | B2 | 12/2001 | McCrory et al. |
| 6,499,488 | B1 | 12/2002 | Hunter et al. |
| 6,565,573 | B1 | 5/2003 | Ferrante et al. |
| 6,582,931 | B1 | 6/2003 | Kois et al. |
| 6,866,666 | B1 | 3/2005 | Sinnott et al. |
| 6,942,667 | B1 | 9/2005 | Song |
| D528,211 | S | 9/2006 | Solar et al. |
| 7,601,000 | B1 | 10/2009 | Hammond |
| 8,170,645 | B2 | 5/2012 | Solar et al. |
| 8,172,573 | B2 | 5/2012 | Sonenfeld et al. |
| 8,185,184 | B2 | 5/2012 | Solar et al. |
| 8,808,000 | B2 | 8/2014 | Salcedo et al. |
| 9,265,590 | B2 | 2/2016 | Zagorchev et al. |
| 9,554,869 | B1 | 1/2017 | Huang et al. |
| 9,877,810 | B2 | 1/2018 | Mozes et al. |
| 9,955,929 | B2 | 5/2018 | Huang et al. |
| 10,022,104 | B2 | 7/2018 | Sell et al. |
| 10,952,814 | B2 | 3/2021 | Kim et al. |
| 2001/0004395 | A1 | 6/2001 | McCrory et al. |
| 2002/0094509 | A1 | 7/2002 | Durbin |
| 2004/0030236 | A1 | 2/2004 | Mazzocchi et al. |
| 2004/0030237 | A1 | 2/2004 | Lee et al. |
| 2004/0167393 | A1 | 8/2004 | Solar et al. |
| 2006/0121409 | A1 | 6/2006 | Olivier |
| 2006/0241406 | A1 | 10/2006 | Noujeim |
| 2008/0234532 | A1 | 9/2008 | De Langen et al. |
| 2013/0172731 | A1 | 7/2013 | Gole |
| 2013/0337400 | A1 | 12/2013 | Yl et al. |
| 2014/0270067 | A1 | 9/2014 | Clark |
| 2014/0379356 | A1 | 12/2014 | Sachdeva |
| 2018/0333231 | A1 | 11/2018 | Somasundaram et al. |
| 2019/0151046 | A1 | 5/2019 | Kim et al. |

FOREIGN PATENT DOCUMENTS

| | | |
|---|---|---|
| WO | WO2007019113 A2 | 2/2007 |
| WO | WO 2019151923 A1 | 8/2019 |

OTHER PUBLICATIONS

Unitek, TAD Temporaty Anchorage Device, 3M Company, St. Paul, MN; www.3m.com/3M/en_US/company-us/all-3m-products/~/Unitek-TADs/?N-5002385+3290412411&preselect-8710666&rl-rud; website; one page plus hyperlinks to related information; publically available and retrieved for viewing on Feb. 4, 2020.

Dentsply, Dentsply Sirona Company, Salzburg, Austria; www dentsplysirona.com; website; 2 pages plus hyperlinks to various dental tools and software, publically available and retrieved for viewing on Feb. 4, 2020.

Dental Wings, Welcome to Dental Wings, Straumann Group Dental Wings Company, Montreal, Quebec, www.dentalwings.com; website; 2 pages plus hyperlinks to various dental software downloads, publically available and retrieved for viewing on Feb. 4, 2020.

3Shape, We Innovate for Superior Patient Care, 3Shape Company, CopenHagen, Denmark, www.3shape.com website, 2 pages plus hyperlinks, publically available and retrieved for viewing on Feb. 4, 2020.

Exocad, Your Future in Digital Dentistry, exocad GmbH Company, Darmstadt, Hessen, www.exocad.com website, 2 pages plus hyperlinks, publically available and retrieved for viewing on Feb. 4, 2020.

International Search Report, issued in connection with PCT/US2021/016917, dated Mar. 29, 2021, 8 pages.

International Search Report, issued in connection with PCT/US2021/012871, dated Mar. 25, 2021, 10 pages.

International Search Report, issued in connection with PCT/US2021/012791, dated Mar. 26, 2021, 10 pages.

Scherer, Michael D.; Presurgical Implant-Site Assessment and Restoratively Driven Digital Planning; Dental Clinics of North America, vol. 58, Issue 3; 35 pages (pp. 561-595); dated Jul. 2014.

DENTAL SCANNING METHODS FOR ANALYZING JAWS

FIELD OF THE DISCLOSURE

This patent generally pertains to dentistry and more specifically to methods of comparing multiple scans for analyzing bite registration and other jaw-related features.

BACKGROUND

A typical jaw of a person or human patient includes a maxilla (upper jaw) and a mandible (lower jaw). Temporamandibular joints (TMJ) allow pivotal and some translational relative movement between the maxilla and mandible, so the person can pivotally open and close their mouth. Both the maxilla and mandible comprise an alveolar bone for supporting teeth. A curved portion of the alveolar bone is known as the alveolar arch, which curves about an oral cavity within the person's mouth. The oral cavity is the space that contains the person's tongue.

Normally, when a person closes their mouth, the teeth in the upper and lower jaws come together in a comfortable engaging relationship known as proper bite registration. Other times, however, malpositioned teeth, missing teeth or interfering dental appliances prevent the jaws from closing in proper bite registration. This can create a number of problems such as stressing the temporamandibular joints, concentrating localized force on certain teeth, and creating a poor visual appearance. Consequently, various dental treatments are used for correcting such problems.

Planning and performing certain dental treatments might first involve creating physical cast models of a patient's upper and lower jaws and analyzing how well the cast models fit together before and after treatment. Some example treatments include installing dentures, repairing dentures, installing implants, applying crowns, jaw surgery, applying braces, and removing teeth.

In some cases, various scanners are used for assisting in the dental treatment process. Some scanners generate a dicom file, which is an acronym for Digital Imaging and Communications in Medicine. Some dicom files have a .dcm file extension.

DETAILED DESCRIPTION

FIGS. 1-27 pertain to a dental scanning method for analyzing jaws of a patient 10 by taking multiple scans of the jaws, and/or models thereof, and then shifting the image of one scan to match that of another. In some examples, fiducial markers are attached to the patient's jaws beforehand to accurately identify and track the relative position of the jaws. The method provides a way for creating a precise image of an upper jaw 12a and a lower jaw 12b in their proper bite registration, even though the resulting image may show an insufficient number of teeth to readily do so. The final, properly shifted image serves as a virtual 3D jaw that can be manipulated and analyzed to aid in various orthodontic and other dental treatments.

Figure 1:
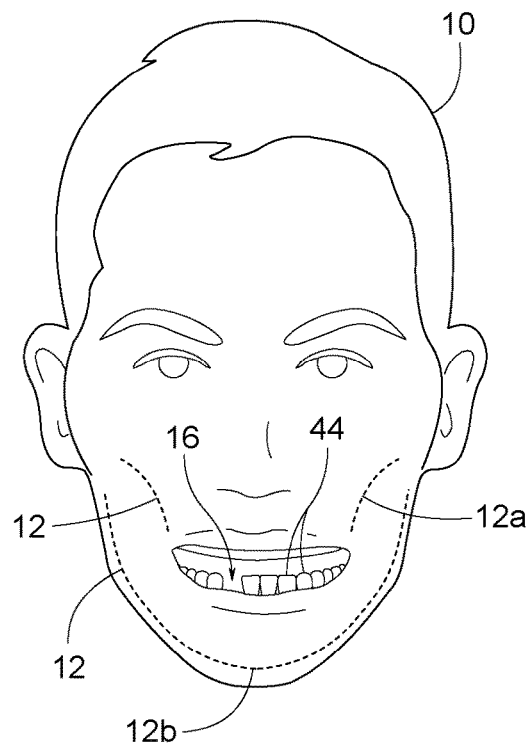
FIG. 1 is a front view of an example patient that has no upper teeth and is missing one lower tooth (illustrative example of a first stage or pretreatment stage).
Figure 2:
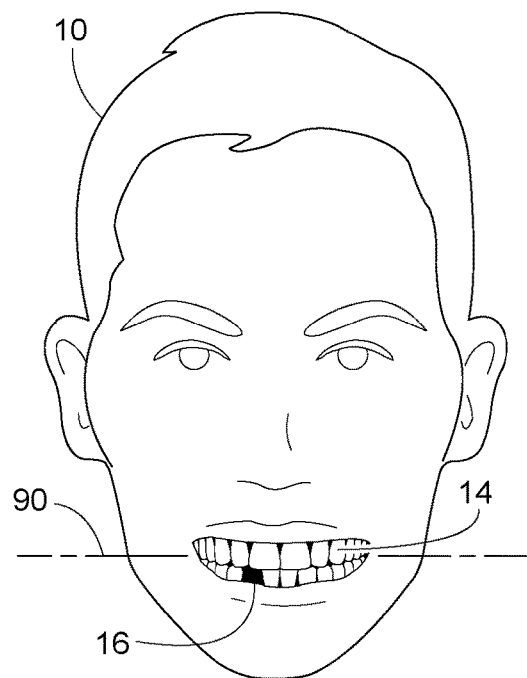
FIG. 2 is a front view of the patient shown in FIG. 1 but with the addition of a poor-fitting upper denture.

The method can be applied to an infinite variety of patients and treatments. Some example treatments include installing dentures, repairing dentures, installing implants, applying crowns, jaw surgery, grinding teeth, shifting teeth, removing teeth, and all other conceivable modifications to the craniofacial complex. For sake of example, the present method can be applied to patient 10, shown in FIGS. 1-3. In this particular example, patient 10 has no upper teeth and is missing a lower tooth, as shown in FIG. 1. Prior to using the method disclosed herein, patient 10 wore an old, poor fitting upper denture 14 and left an area 16 of the missing lower tooth open, as shown in FIG. 2.

Figure 3:
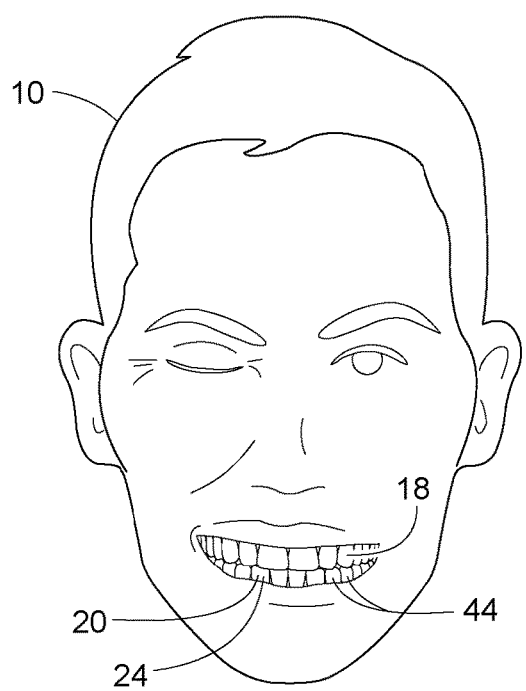
FIG. 3 is a front view of the patient shown in FIG. 1 but with the addition of a new upper denture and an implant replacing the missing lower tooth.

Following treatment, patient 10 is provided with a well fitting upper denture 18 plus an implant 20 to fill the space of the missing tooth, as shown in FIG. 3. The term, "implant" refers to an anchor 22 attached to a jaw bone and/or a crown 24 attached to anchor 22. Some example implants further include a post 26 (e.g., a screw, a rod, a pin, etc.) for fastening crown 24 to anchor 22.

Patient 10 has two jaw members 12 including upper jaw 12a (maxilla) and lower jaw 12b (mandible). The term, "first jaw" refers to either jaw, the maxilla or the mandible. Likewise, the term, "second jaw" refers interchangeably to the maxilla or mandible. FIGS. 4-7, 11 and 12 show the patient's actual jaw members 12, not models thereof. FIGS. 4-7 show jaws 12a and 12b in the condition similar to that shown in FIG. 2, wherein old denture 14 is on upper jaw 12a and space 16 is left empty.

To provide jaw 12a and/or jaw 12b with reference points that help identify the jaws' relative location and orientation in later scanned images of jaws 12a and 12b, some example methods involve installing multiple fiducial markers 28 into an alveolar bone 30 (FIGS. 8 and 9) of jaw 12a and/or 12b. The term, "alveolar bone" refers to the bony structure of either jaw 12a or 12b. The term, "fiducial marker" refers to any item that includes a substantially radiopaque feature.

Figure 25:
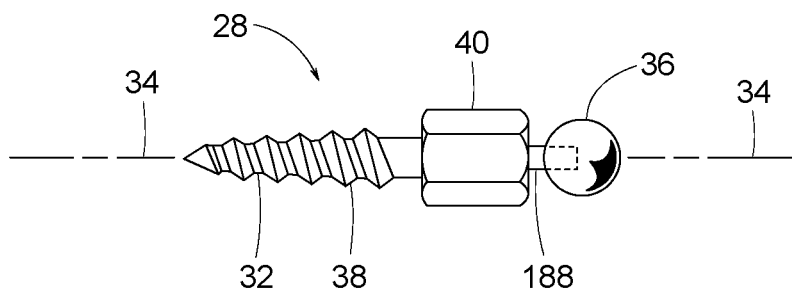
FIG. 25 is a side view of an example fiducial marker constructed in accordance with the teachings disclosed herein.
Figure 26:
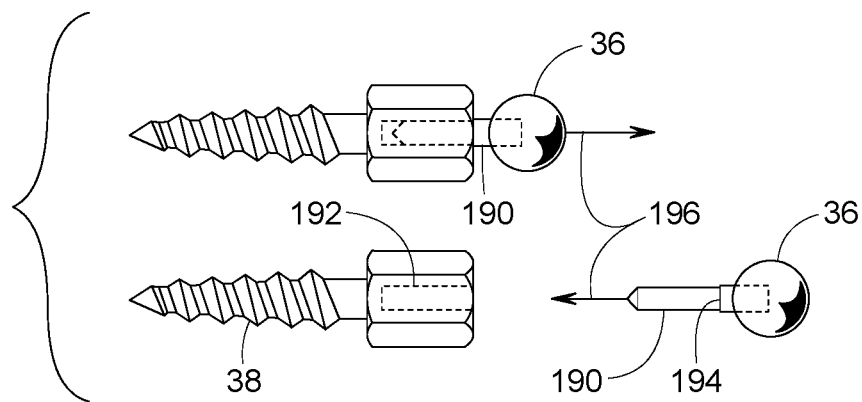
FIG. 26 are side views of another example fiducial marker constructed in accordance with the teachings disclosed herein.
Figure 27:
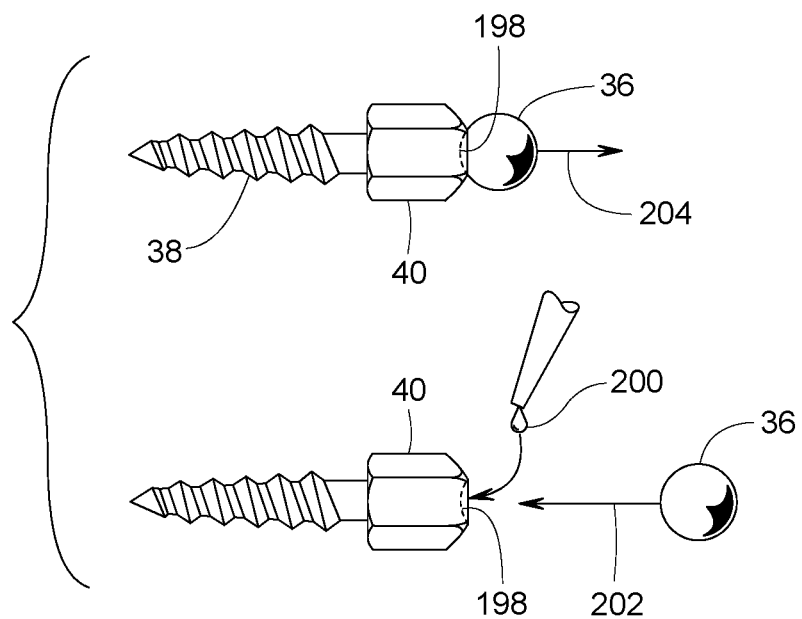
FIG. 27 are side views of yet another example fiducial marker constructed in accordance with the teachings disclosed herein.

Some examples of fiducial marker 28 comprise a shaft 32 extending along a longitudinal axis 34 from a marker body 36. The term, "shaft" refers to any elongate member that is generally cylindrical, tapered and/or threaded. Some examples of shaft 32 include a screw, a straight pin, a tapered pin, a rod, a nail, etc. In the illustrated examples, shaft 32 is a screw 38. The term, "marker body" refers to any structure of any shape that is substantially radiopaque. In some examples, marker body 36 is generally spherical and made of a polymer with 10% barium sulfate. In some examples, marker body 36 is overmolded or otherwise attached to a head 40 of screw 38. Some examples of screw 38 are made of a generally noncorrosive material, such as stainless steel, carbide or titanium. Head 40, in some examples, has a tool-mating geometry, so screw 38 can be readily driven into jaw member 12. Various examples of fiducial marker 28 are shown in FIGS. 25-27 and will be described later in more detail.

Figure 4:
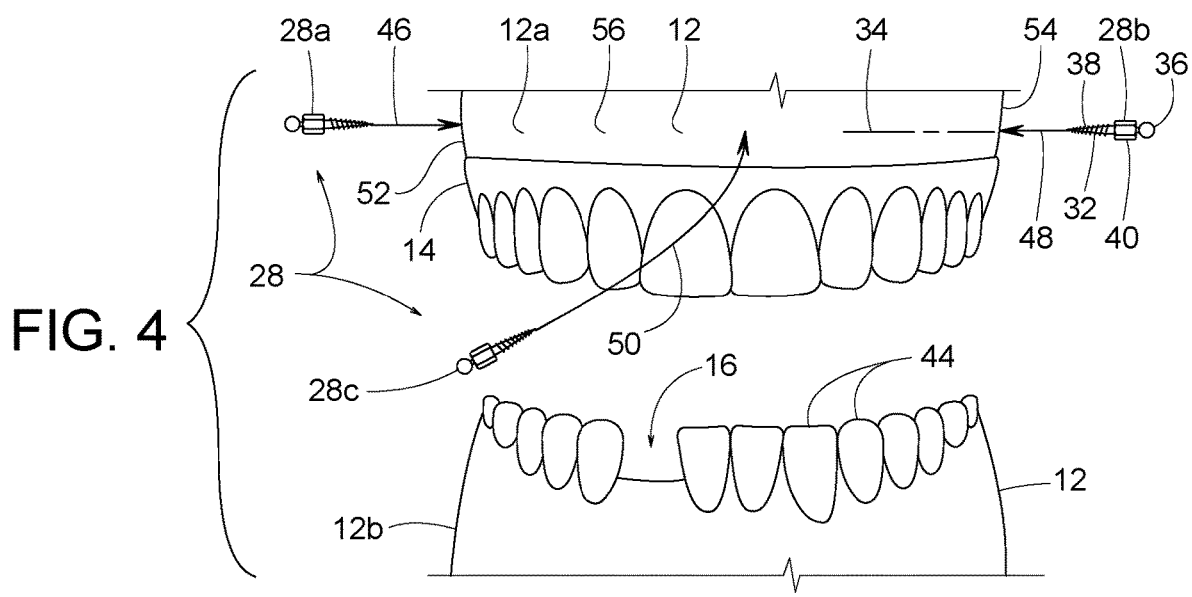
FIG. 4 is a front view of the patient's upper and lower jaws with fiducial markers being installed in the upper jaw, just above the poor-fitting upper denture.
Figure 5:
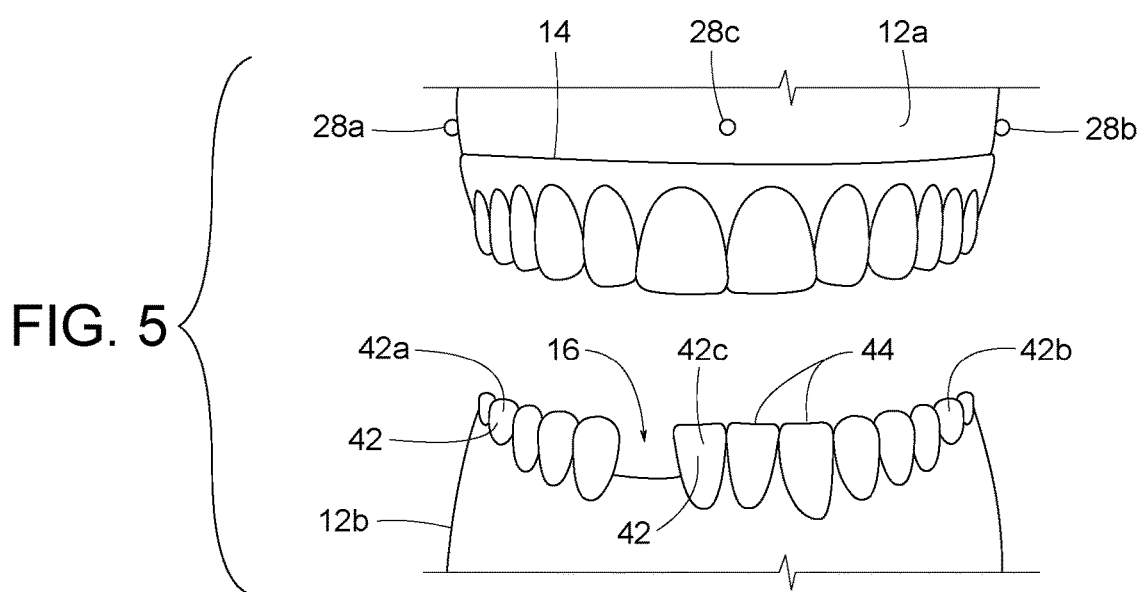
FIG. 5 is a front view similar to FIG. 4 but showing the fiducial markers already installed.

For minimal invasiveness, in some examples, markers 28 are only installed in one of jaw members 12, as shown in FIGS. 4 and 5, and distinct stable features 42 of teeth 44 are used as reference points on the other jaw member 12. Some examples of features 42 include chosen edges, corners, faces, and peaks of individual teeth 44 or a dental appliance supported by one of the jaws 12. More specific examples include a first feature 42a (face of a first chosen tooth), a second feature 42b (face of a second chosen tooth), and a third feature 42c (face of a third chosen tooth).

In the example shown in FIGS. 4 and 5, fiducial markers 28 include a right fiducial marker 28a, a left fiducial marker 28b, and a front fiducial marker 28c. Arrows 46, 48 and 50 respectively represent attaching right fiducial marker 28a to a right portion 52 of first jaw 12a, attaching left fiducial marker 28b to a left portion 54 of first jaw 12a, and attaching front fiducial marker 28c to a front portion 56 of first jaw 12a. FIG. 5 shows markers 28a, 28b and 28c in their installed positions. Such a spread-out arrangement of three markers 28 provides upper jaw 12a with a broad footprint for maximum positional accuracy.

Figure 6:
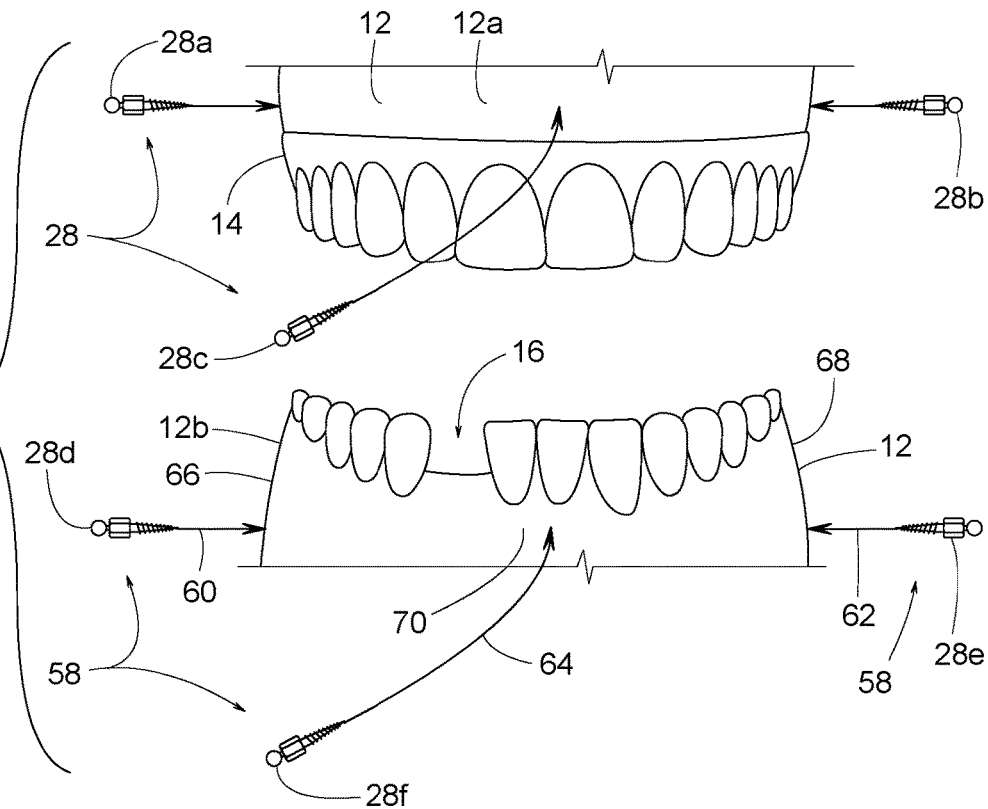
FIG. 6 is a front view similar to FIG. 4 but showing fiducial markers being installed in both the upper and lower jaws.
Figure 7:
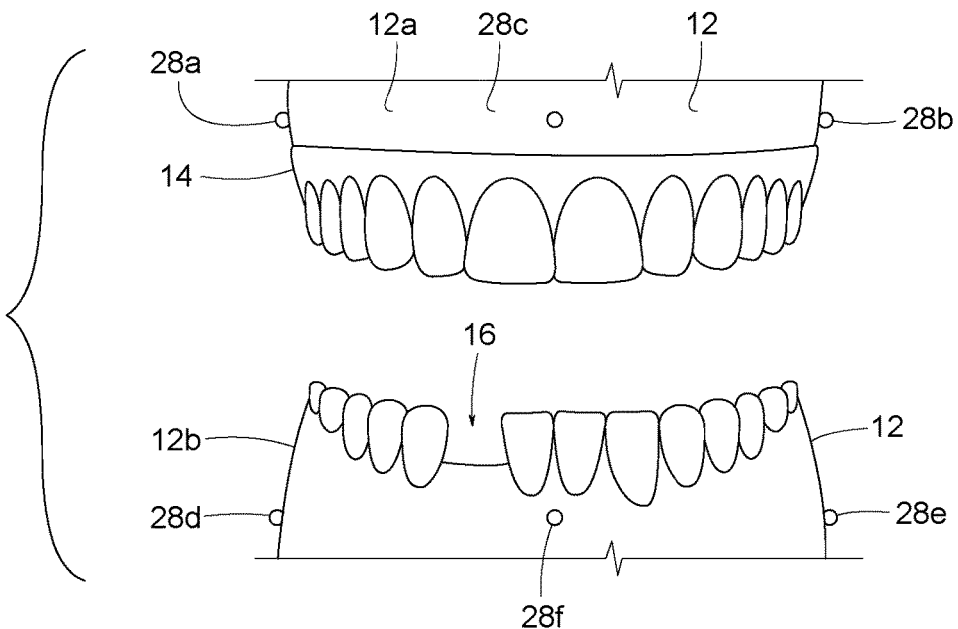
FIG. 7 is a front view similar to FIG. 6 but showing the fiducial markers already installed.

In addition or alternatively, FIGS. 6 and 7 show the installation of a second set 58 of three fiducial markers 28 comprising a right fiducial marker 28d, a left fiducial marker 28e, and a front fiducial marker 28f. Arrows 60, 62 and 64 respectively represent attaching left fiducial marker 28d to a right portion 66 of second jaw 12b, attaching left fiducial marker 28e to a left portion 68 of second jaw 12b, and attaching front fiducial marker 28f to a front portion 70 of second jaw 12b. FIG. 6 shows markers 28d, 28e and 28f in their installed positions.

In some examples, the second set 58 of fiducial markers 28 provides a more precise indication of the second jaw's location and orientation than what is otherwise achieved by relying instead on distinct features 42 of teeth 44. This is because markers 28d, 28e, and 28f can be more spread out than teeth 44, and the size of marker bodies 36 is usually smaller than teeth 44.

Figure 8:
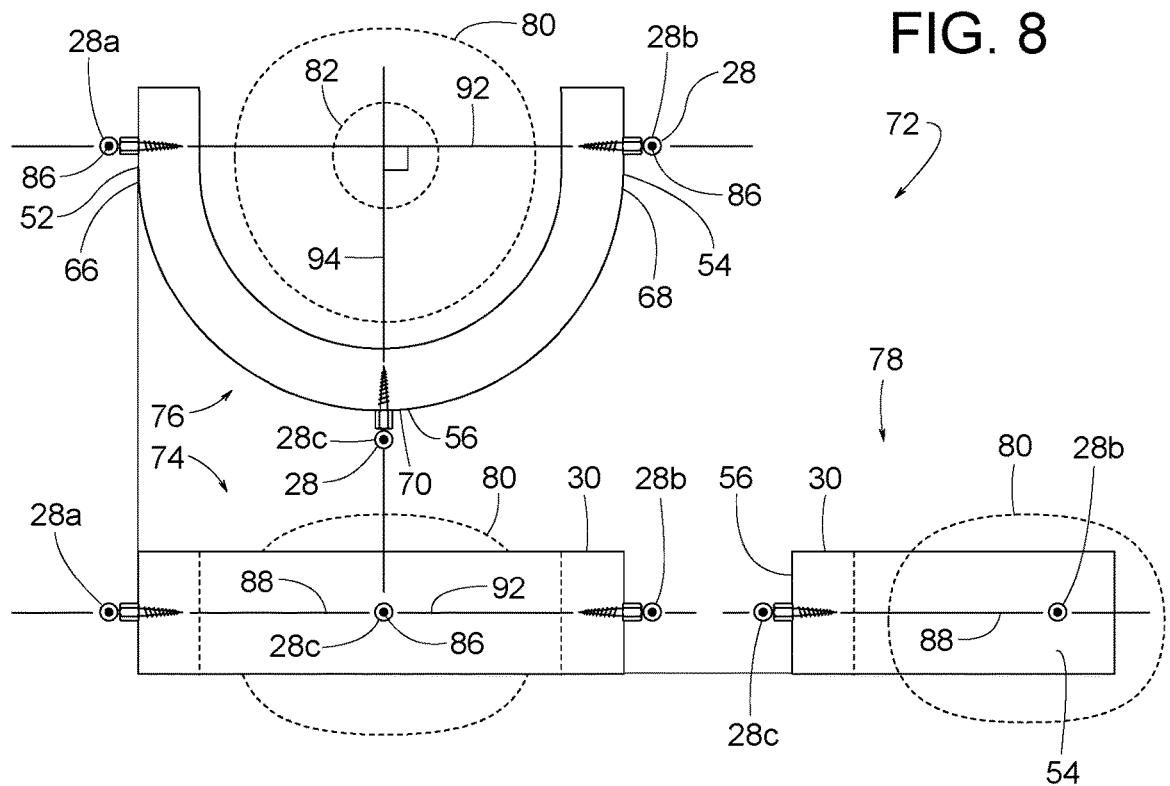
FIG. 8 is a set of orthogonal views showing an example scanning arrangement of fiducial markers screwed into in a schematically illustrated alveolar bone of either an upper or lower jaw.
Figure 9:
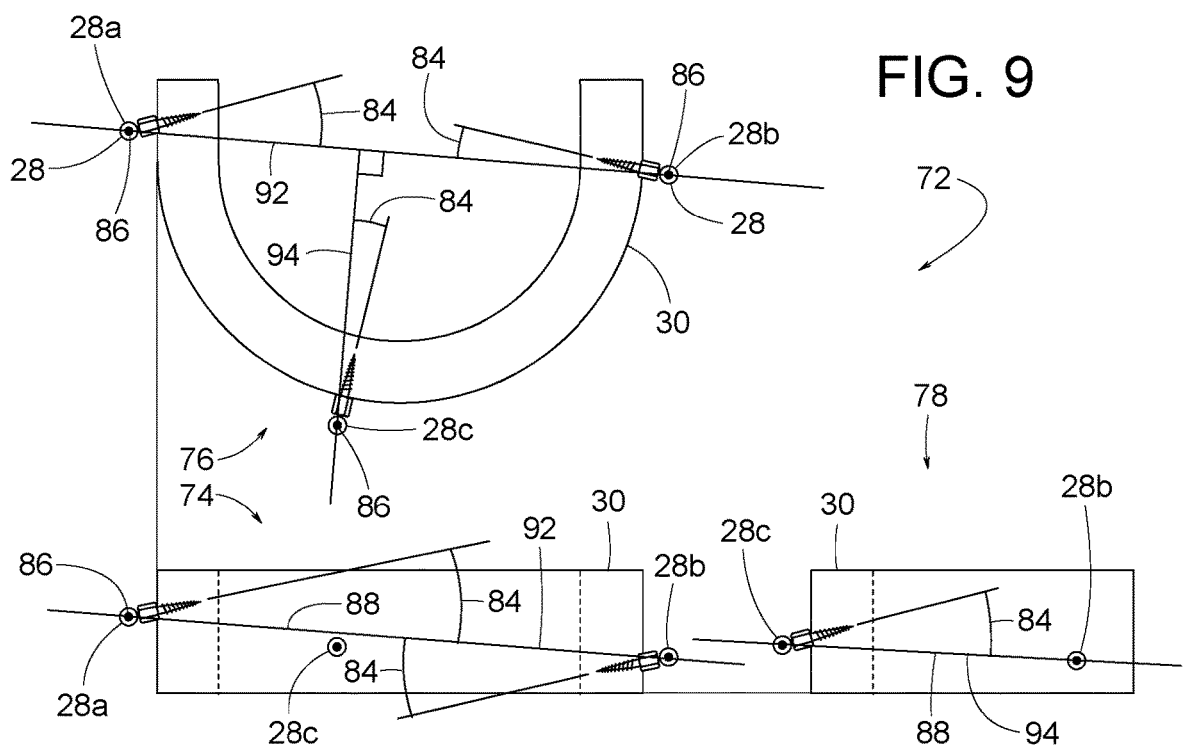
FIG. 9 is a set of orthogonal views showing another example scanning arrangement of fiducial markers screwed into in a schematically illustrated alveolar bone of either an upper or lower jaw.

FIGS. 8 and 9 are sets of orthogonal views showing example scanning arrangements 72 of fiducial markers 28 screwed into in a schematically illustrated alveolar bone 30 of either jaw member 12. FIG. 8 shows a front view 74, a top view 76, and a right side view 78 of jaw member 12 with fiducial markers 28 in an ideal arrangement. FIG. 9 shows the same views 74, 76 and 78 but with fiducial markers 28 in a more misaligned yet still acceptable configuration. From a vertical perspective, as shown in top view 76 of FIGS. 8 and 9, fiducial markers 28 extend beyond the general outer perimeter of jaw member 12 (i.e., outer perimeter in the vicinity of markers 28). Fiducial markers 28 thus provide a broader footprint for greater positional accuracy, as mentioned earlier.

FIGS. 8 and 9 show fiducial markers 28 and alveolar bone 30 in relation to an oral cavity 80 of patient 10. Oral cavity 80 is the area surrounded by alveolar bone 30. In the illustrated examples, screw 38 of each of the three fiducial markers 28 points inward toward a central region 82 of oral cavity 80 when fiducial markers 28 are attached to alveolar bone 30.

In some examples, for maxilla 12a, fiducial marker 28c is installed just below the midline of the anterior nasal spine, at the end of the superior labial frenulum. In some examples, fiducial markers 28a and 28b are installed just anterior of the maxillary tuberosity, with marker 28a on the right side and marker 28b on the left side.

In some examples, for mandible 12b, fiducial marker 28f is installed in the medial border of the hemi-mandible, near the alveolar crest. In some examples, fiducial markers 28d and 28e are installed along the oblique line, just below the posterior-most teeth, with marker 28d on the right side and marker 28e on the left side.

It has been discovered that the arrangements shown in FIGS. 8 and 9 provide good results when each fiducial marker's angular deviation (angle 84) is within 45 degrees of a predetermined ideal layout. More specifically, in the illustrated examples, each marker body 28 defines a center point 86 and are arranged such that:
a) center points 86 of fiducial markers 28a, 28b and 28c define a plane 88 (in some examples, plane 88 is generally parallel to an occlusal plane 90 of patient 10);
b) center point 86 of left fiducial marker 28b and center point 86 of right fiducial marker 28a define a lateral line 92 intersecting center point 86 of left fiducial marker 28b and center point 86 of right fiducial marker 28a;
c) center point 86 of front fiducial marker 28c defines a forward line 94 intersecting center point 86 of front fiducial marker 28c, intersecting lateral line 92, and being perpendicular to lateral line 92;
d) shaft 32 of left fiducial marker 28b lies within an angle 84 of 45 degrees of lateral line 92 as viewed from a direction perpendicular to plane 88;
e) shaft 32 of left fiducial marker 28b lies within an angle 84 of 45 degrees of lateral line 92 as viewed from a direction parallel to plane 88 and perpendicular to lateral line 92;
f) shaft 32 of right fiducial marker 28a lies within an angle 84 of 45 degrees of lateral line 92;
g) shaft 32 of right fiducial marker 28a lies within an angle 84 of 45 degrees of lateral line 92 as viewed from a direction parallel to plane 88 and perpendicular to lateral line 92;
h) shaft 32 of front fiducial marker 28c lies within an angle 84 of 45 degrees of forward line 94; and
i) shaft 32 of front fiducial marker 28c lies within an angle 84 of 45 degrees of lateral line 92 as viewed from a direction parallel to plane 88 and perpendicular to lateral line 92.

Figure 10:
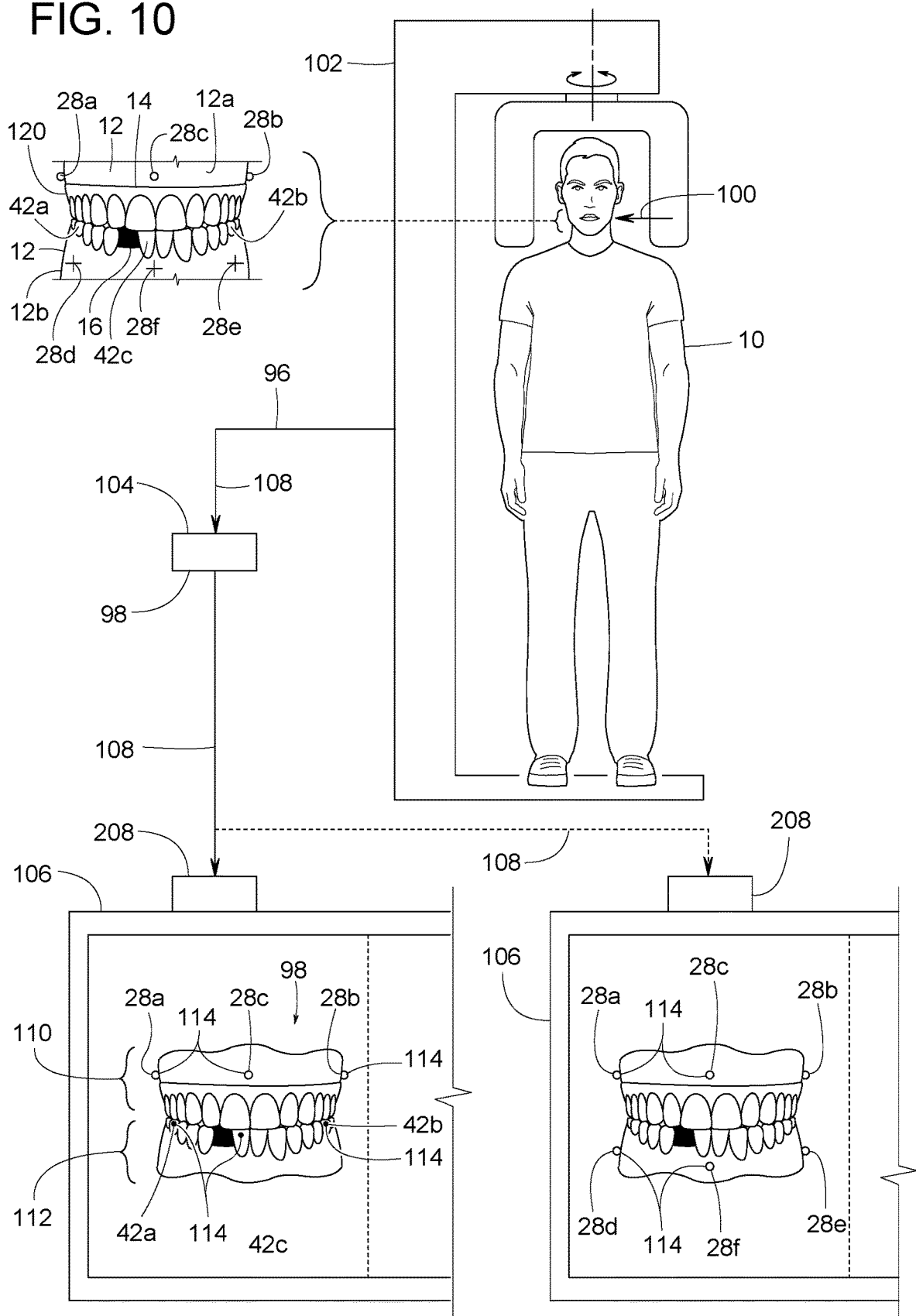
FIG. 10 is a schematic diagram illustrating various method steps associated with a first scanning machine (illustrative example of a second stage or CT stage).

In the example shown in FIGS. 4, 5 and 10, three fiducial markers 28a, 28b and 28c in upper jaw 12a and three features 42a, 42b and 42c of lower jaw 12b will be used as clear, distinct reference points for marking the location of upper jaw 12a relative to lower jaw 12b. Further steps in some examples of the present dental scanning method will now be explained with reference to FIGS. 10-24.

FIG. 10 illustrates creating 96 a first scan result 98 by scanning 100 first jaw 12a, second jaw 12b; three fiducial markers 28a, 28b and 28c on first jaw 12a; and three features 42a, 42b and 42c on second jaw 12b. In some examples, first scan result 98 is created by scanning 100 fiducial markers 28d, 28e and 28f in addition or alternatively to capturing features 42a, 42b and 42c.

In either case, scanning 100 is done while jaws 12 are in a predetermined target bite position relative to each other. In some examples, the predetermined target bite position is referred to as a proper bite registration, wherein the teeth and/or other installed dental appliances fit comfortably together in a generally closed position without subjecting the temporamandibular joints to undo stress. An example of such a predetermined target bite position, or proper bite registration, is shown in FIG. 2 and the upper left corner of FIG. 10.

The term, "dental appliance" refers to any device temporarily or permanently installed within a patient's mouth. Some example dental appliances include full dentures, partial dentures, bridges, crowns, cavity fillings, braces, implants, etc. In some examples, dental appliances and a patient's actual teeth are some examples of "spacers," as both teeth and dental appliances limit how closely upper jaw 12a and lower jaw 12b can come together.

Scanning 100, as shown in FIG. 10, can be done by any suitable scanning method. Some example methods of scanning 100 include cone beam computed tomography (CBCT), magnetic resonance imaging (MRI), computed tomography (CT or CAT), X-ray, etc. In some examples, scanning 100 is performed using a CBCT scanning machine 102 (first scanning machine 102). Some examples of first scanning machine 102 include an i-Cat FLX.I cone beam 3D imaging scanner manufactured by Imaging Sciences International LLC of Alpharetta, Ga. or Hatfield, Pa.

From first scanning machine 102, first scan result 98 is transferred in a file format 104 to a computer 106, as indicated by arrows 108 of FIG. 10. In some examples, first scanning machine 102 generates first scan result 98 in a first format (e.g., a dicom file), and computer 106 converts the first format to a more manageable digital format (e.g., an stl file). In some examples, the file conversion is accomplished through dental treatment planning software executed by computer 106. Some examples of such software include exocad, 3shape, dental wings, and Dentsply Sirona. In other examples, first scanning machine 102 generates first scan result 98 directly in a more manageable digital format without the need for subsequent file conversion by computer 106.

FIG. 10 also shows computer 106 displaying first scan result 98 including a first scanned representation of the first jaw 110, a first scanned representation of the second jaw 112, and a first constellation of points 114. In some examples, first constellation of points 114 represents three fiducial markers 28a, 28b and 28c; as shown in the left-bottom of FIG. 10. In some examples, first constellation of points 114 represents three fiducial markers 28a, 28b and 28c on first jaw 12a plus three features 42a, 42b and 42c on second jaw 12b; also shown in the left-bottom of FIG. 10. In some examples, first constellation of points 114 represents three fiducial markers 28a, 28b and 28c on first jaw 12a plus second set 58 of three fiducial markers 28d, 28e and 28f on second jaw 12b; shown in the right-bottom of FIG. 10.

First scan result 98, regardless of which example of first constellation of points 114 is being used, provides a reference against which subsequent scans will be compared. Such later scans will be used for creating an accurate digital jaw model 116 (FIGS. 20, 23 and 24) that can be manipulated and analyzed in the treatment of patient 10. Various method steps for producing such scans are shown in FIGS. 11-14.

Figure 11:
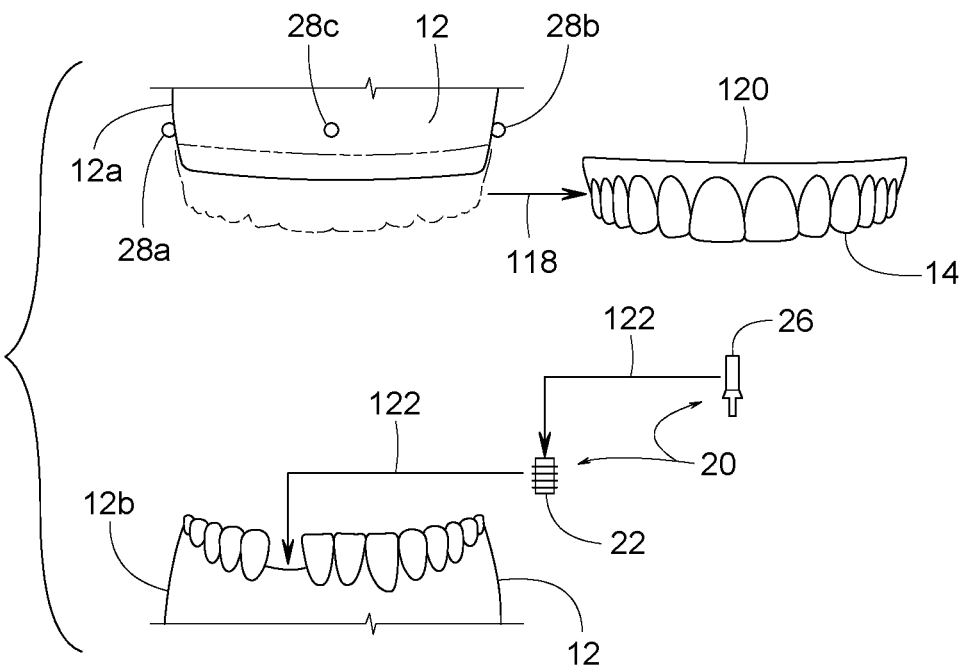
FIG. 11 is a front view showing example dental appliances being added and removed from the patient as shown in FIG. 2.
Figure 14:
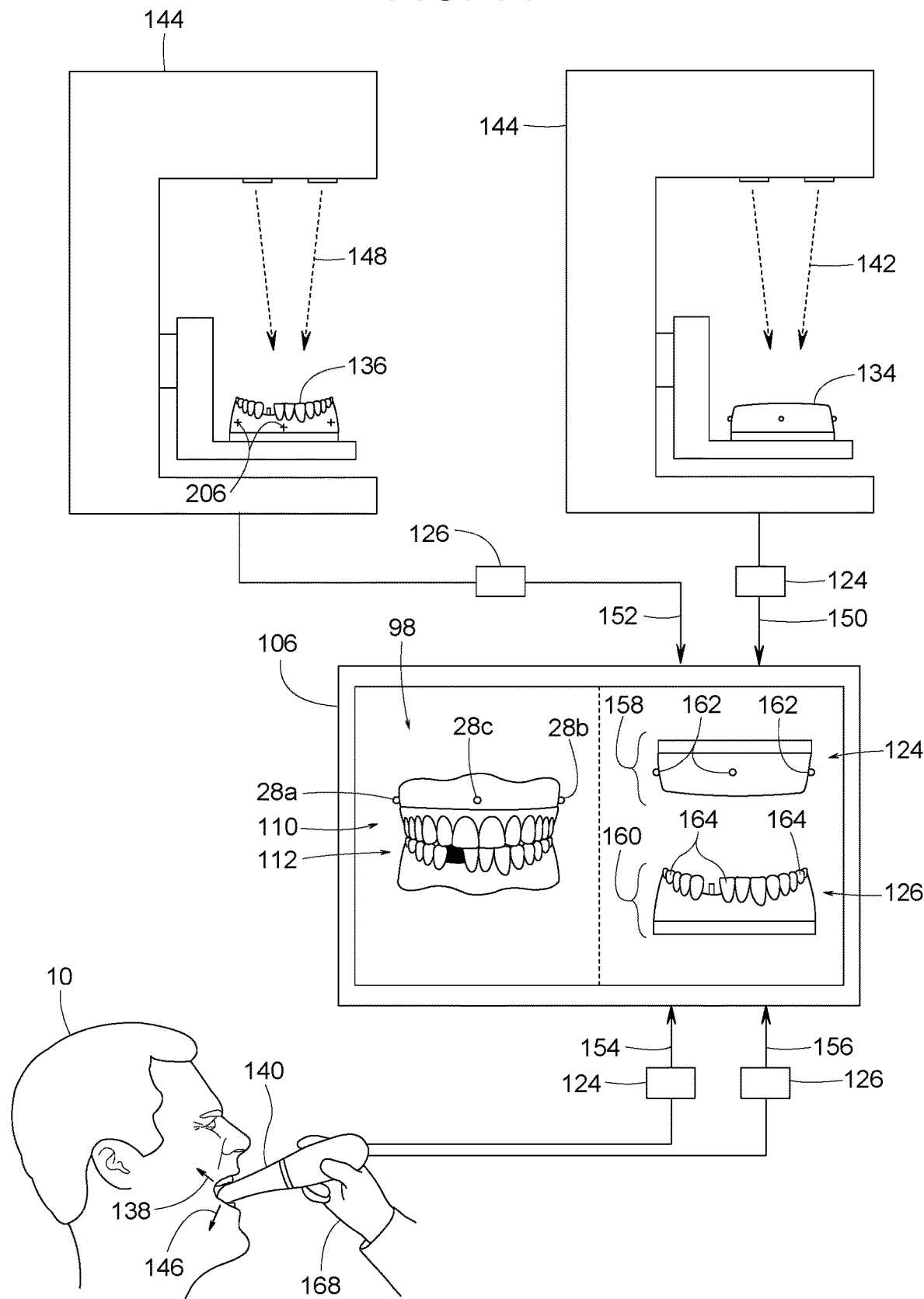
FIG. 14 is a schematic diagram showing additional example scanning methods (illustrative example of a third stage or surface scan stage).

Arrow 118 of FIG. 11 represents old dentures 14 being removed from the patient's upper jaw 12a. Since dentures 14 limit how closely jaws 12 can close, dentures 14 are considered as being a spacer 120, and arrow 118 represents removing spacer 120 from patient 10. In this example, arrows 122 represent attaching implant 20 (e.g., anchor 22 and post 26) to lower jaw 12b, thus arrows 122 more broadly represent attaching implant 20 to at least one of first jaw 12a and second jaw 12b and doing so after creating first scan result 98 (FIG. 10) but before creating at least one of a second scan result 124 (FIG. 14) and a third scan result 126 (FIG. 14). FIG. 10, on the other hand, shows jaws 12 being scanned while spacer 120 (e.g., old dentures 14) are still in place to help position jaws 12 at the predetermined target bite position for proper bite registration.

Figure 12:
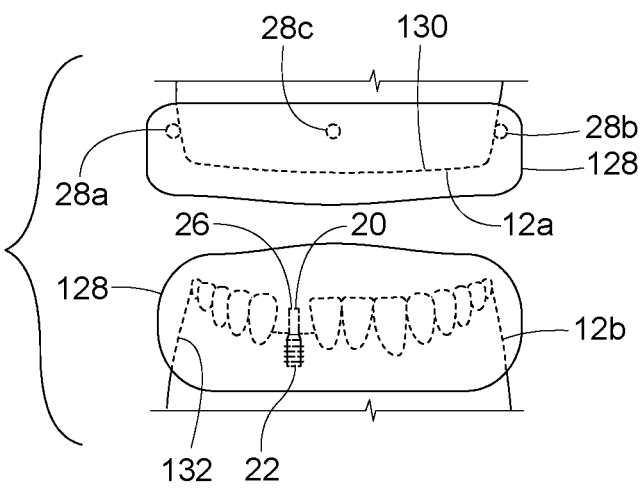
FIG. 12 is a front view showing an example method for creating cast models of the patient's jaws after the addition or removal of example dental appliances.

FIG. 12 illustrates a conventional method of using a known molding material 128 for creating molds 130 and 132 of jaws 12a and 12b, respectively. In this example, molds 130 and 132 capture the contours of jaws 12a and 12b including the shapes of implant 20; markers 28a, 28b and 28c; features 42a, 42b and 42c; the void due to the omission of dentures 14; and markers 28d, 28e and 28f (if used). Molds 130 and 132, however, can be independent of each other, so they do not necessarily capture the relative positions of jaws 12a and 12b.

Figure 13:
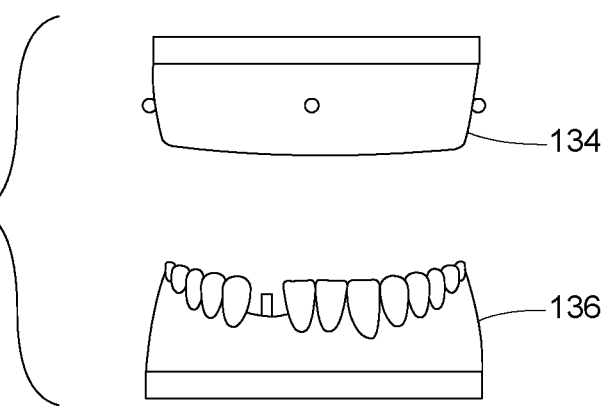
FIG. 13 is a front view of cast models created by the method shown in FIG. 12.

Molds 130 and 132 produce a physical model 134 of first jaw 12a and a physical model 136 of second jaw 12b, as shown in FIG. 13. In some examples, models 134 and 136 are castings created within the mold cavities of molds 130 and 132. Such methods of creating physical models 134 and 136 are well known to provide accurate reproductions of the surface geometries of jaws 12.

FIG. 14 illustrates creating second scan result 124 by scanning 138 first jaw 12a directly via a scanner 140 or scanning 142 the physical model 134 of first jaw 12a via a scanner 144. FIG. 14 also illustrates creating third scan result 126 by scanning 146 second jaw 12b directly via scanner 140 or scanning 148 the physical model 136 of second jaw 12b via scanner 144. Some examples of scanner 140 include a Carestream CS3600 intraoral scanner provided by Carestream Dental LLC of Rochester, N.Y. or Atlanta, Ga. Some examples of scanner 144 include a Medit Identica T500 benchtop scanner of Seoul, South Korea.

In some examples, using scanner 144 for scanning models 134 and 136 provides a sharper, more distinct image of individual jaws 12a and 12b than what can be achieved with scanner 102 (FIG. 10). Scanner 102, however, provides a clear representation of the jaws' relative position in their natural bite registration. So, there is a benefit to using both scanners 102 and 144, wherein scanner 102 is an example of a first scanning machine, scanner 144 is an example of a second scanning machine, and scanners 102 and 144 are two different scanning machines.

Using intraoral scanner 140 for scanning jaws 12 directly is an alternative to using scanner 144. Scanner 140 eliminates the need for creating models 134 and 136; however, scanner 140 might accumulate a series of incremental positional errors while traversing a significant distance across jaws 12. Both scanners 140 and 144 are considered "second scanning machines" and each one is different than first scanning machine 102.

Regardless of which second scanning machine 140 or 144 is used, scanners 140 and 144 generate second scan result 124 representing upper jaw 12a and third scan result 126 representing lower jaw 12b. Arrow 150 represents transmitting second scan result 124 of upper jaw model 134 from scanner 144 to computer 106, arrow 152 represents transmitting third scan result 126 of lower jaw model 136 from scanner 144 to computer 106, arrow 154 represents transmitting second scan result 124 of upper jaw 12a to computer 106, and arrow 156 represents transmitting third scan result 126 of lower jaw 12b to computer 106.

In response to receiving scan information from scanner 140 or 144, computer 106 displays second scan result 124 and third scan result 126, as shown in FIG. 14. Second scan result 124 includes a second scanned representation of the first jaw 158 and a second constellation of points 162 representing the three fiducial markers 28a, 28b and 28c. Third scan result 126 includes a second scanned representation of the second jaw 160. In some examples, third scan result 126 further includes a third constellation of points 164 representing features 42a, 42b and 42c and/or representing the second set of fiducial markers 28d, 28e and 28f.

In some examples, the first constellation of points 114, the second constellation of points 162, and/or the third constellation of points 164 are used as reference points in shifting the individual jaw images in the second scan to match the properly fitting jaw image in the first scan. In other words, shifting second scanned representation of the first jaw 158 (e.g., upper jaw 12a) relative to second scanned representation of the second jaw 160 (e.g., lower jaw 12b) so they align with first scanned representation of the first jaw 119 (e.g., upper jaw 12a) and first scanned representation of the second jaw 112 (e.g., lower jaw 12b). The goal is to shift the sharp, clear individual jaw images of jaws 12a and 12b in the second scan (FIG. 14) according to the bite registration of the first scan (FIG. 10) to create the precise digital jaw model 116 (FIGS. 20, 23 and 24) that can be manipulated and analyzed to aid in various orthodontic and other dental treatments.

FIGS. 15-20 illustrate an example of creating digital jaw model 116 (FIG. 20) by shifting (arrows 166 of FIG. 19) the second scanned representation of the first jaw 158 relative to second scanned representation of the second jaw 160 such that the second constellation of points 162 relative to the second scanned representation of the second jaw 160 substantially coincides with the first constellation of points 114 relative to the first scanned representation of the second jaw 112.

In some examples, creating an association of fiducial markers 28 and/or features 42 in the second and third scan results 124 and 126 and the corresponding fiducial markers 28 and/or features 42 in the first scan result 98, involves a dental practitioner 168 (e.g., a dentist, a lab technician, etc.) manually identifying via mouse-clicking 170 on select pairs of points of constellations 114, 162 and 164 for which associations are to be established. Constellations 114, 162 and 164 each comprise a plurality of individual points 172. Mouse-clicking 170 is one example method for manually identifying where the plurality of individual points 172 are located in space (e.g., identifying their coordinates) and for determining how far at least some of the plurality of individual points 172 should be shifted.

Figure 21:
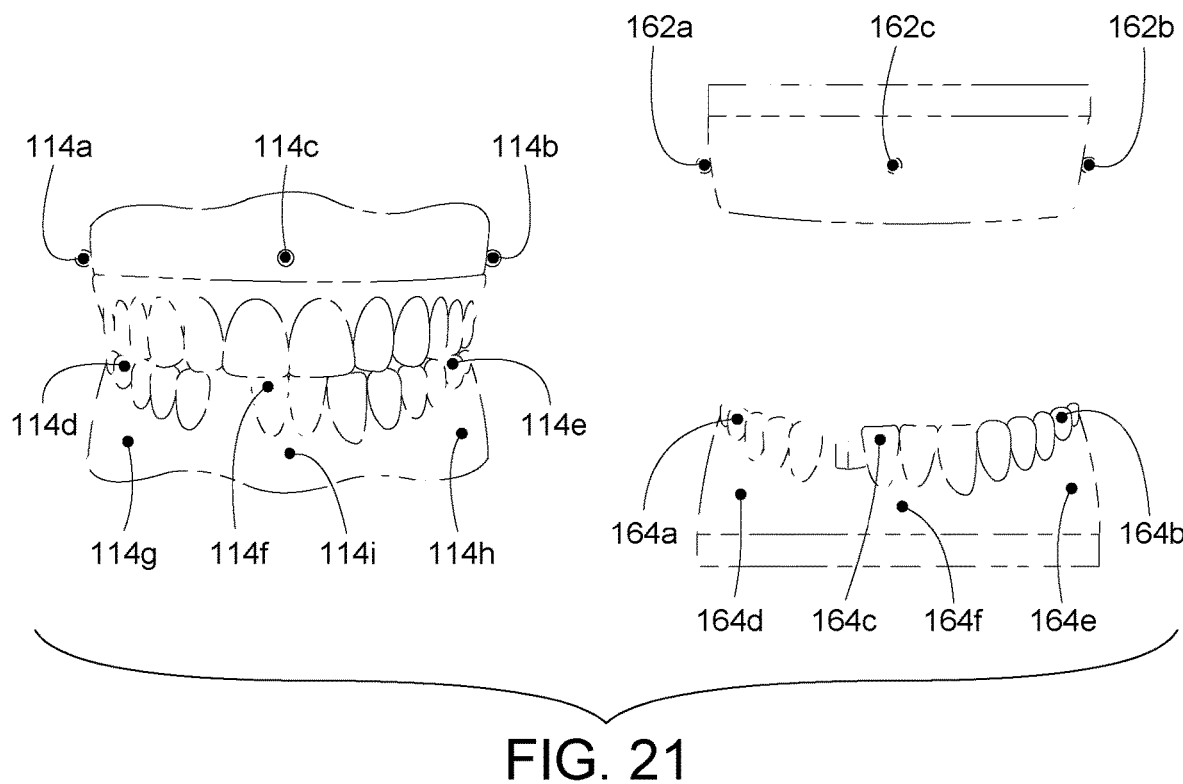
FIG. 21 is a front view of example jaw images that include some example constellations of points (another illustrative example of a fourth stage or registration stage).

In some examples, referring to FIG. 21, first constellation of points 114 includes points 114a, 114b and 114c, which correspond to fiducial markers 28a, 28b and 28c, respectively. In addition or alternatively, some examples of first constellation of points 114 includes points 114d, 114e and 114f, which correspond to features 42a, 42b and 42c, respectively. In addition or alternatively, some examples of first constellation of points 114 includes points 114g, 114h and 114i, which correspond to fiducial markers 28d, 28e and 28f, respectively.

In some examples, second constellation of points 162 includes points 162a, 162b and 162c, which correspond to fiducial markers 28a, 28b and 28c, respectively.

In some examples of third constellation of points 164 includes points 164a, 164b and 164c, which correspond to features 42a, 42b and 42c, respectively. In addition or alternatively, some examples of third constellation of points 164 includes points 164d, 164e and 164f, which correspond to fiducial markers 28d, 28e and 28f, respectively.

In some examples, a composite constellation of points 174 comprises a combination of the second and third constellation of points 162 and 164. Some examples of the composite constellation of points 174 include points 162a, 162b and 162c plus points 164a, 164b and 164c. Some examples of the composite constellation of points 174 include points 162a, 162b and 162c plus points 164d, 164e and 164f.

Figure 15:
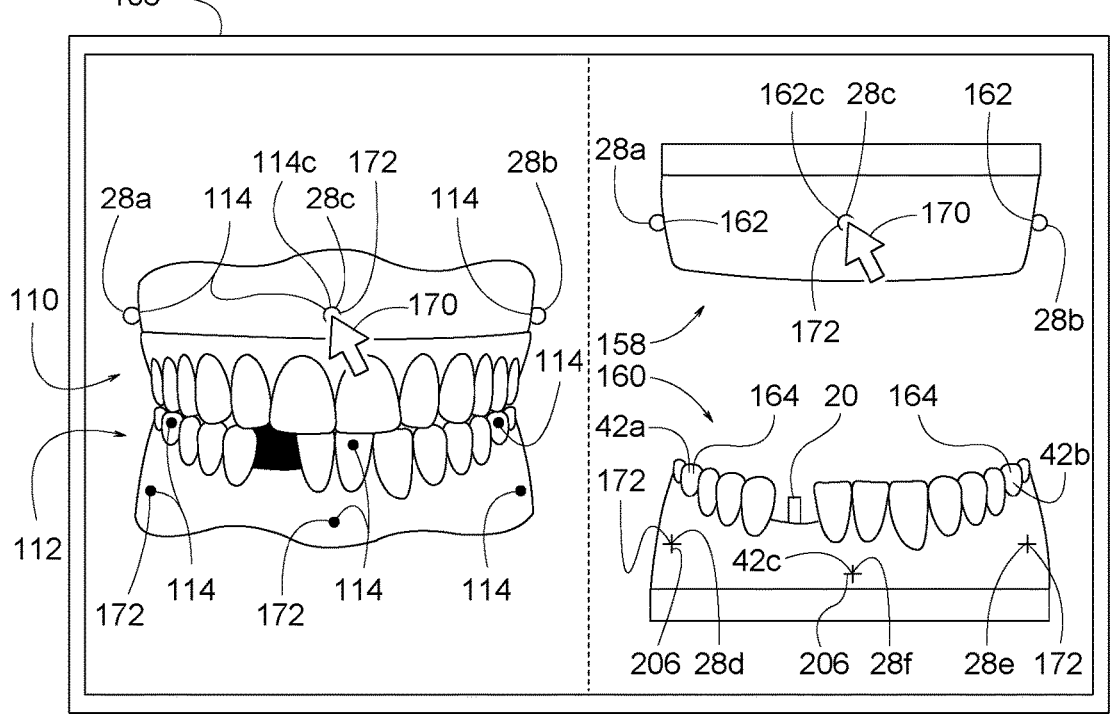
FIG. 15 is front view of a computer displaying multiple scan results of jaws and a schematic depiction of a dental practitioner mouse-clinking on certain points of the scan results (illustrative example of a fourth stage or registration stage).

FIG. 15 illustrates mouse-clicking 170 on point 114c of first constellation of points 114 and mouse-clicking 170 on point 162c of second constellation of points 162. In response to such mouse-clicking, computer 106 determines that points 114c and 162c represent the same point (marker 28c) on first jaw 12a.

Figure 16:
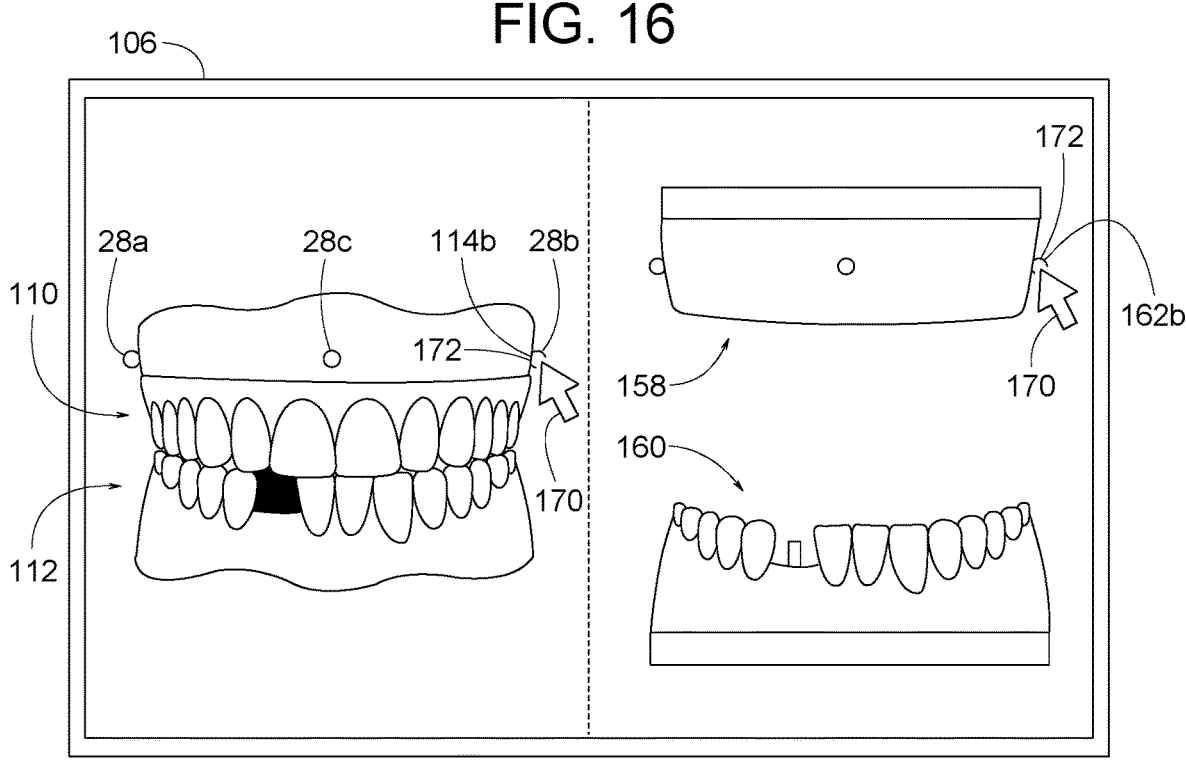
FIG. 16 is front view similar to FIG. 15 but showing a schematic depiction of the dental practitioner mouse-clinking on other points of the scan results (another illustrative example of a fourth stage or registration stage).

FIG. 16 illustrates mouse-clicking 170 on point 114b of first constellation of points 114 and mouse-clicking 170 on point 162b of second constellation of points 162. In response to such mouse-clicking, computer 106 determines that points 114b and 162b represent the same point (marker 28b) on first jaw 12a.

Likewise, similar mouse-clicking on point 114a of first constellation of points 114 and mouse-clicking 170 on point 162a of second constellation of points 162 is interpreted as meaning that points 114a and 162a represent the same point (marker 28a) on first jaw 12a.

Figure 17:
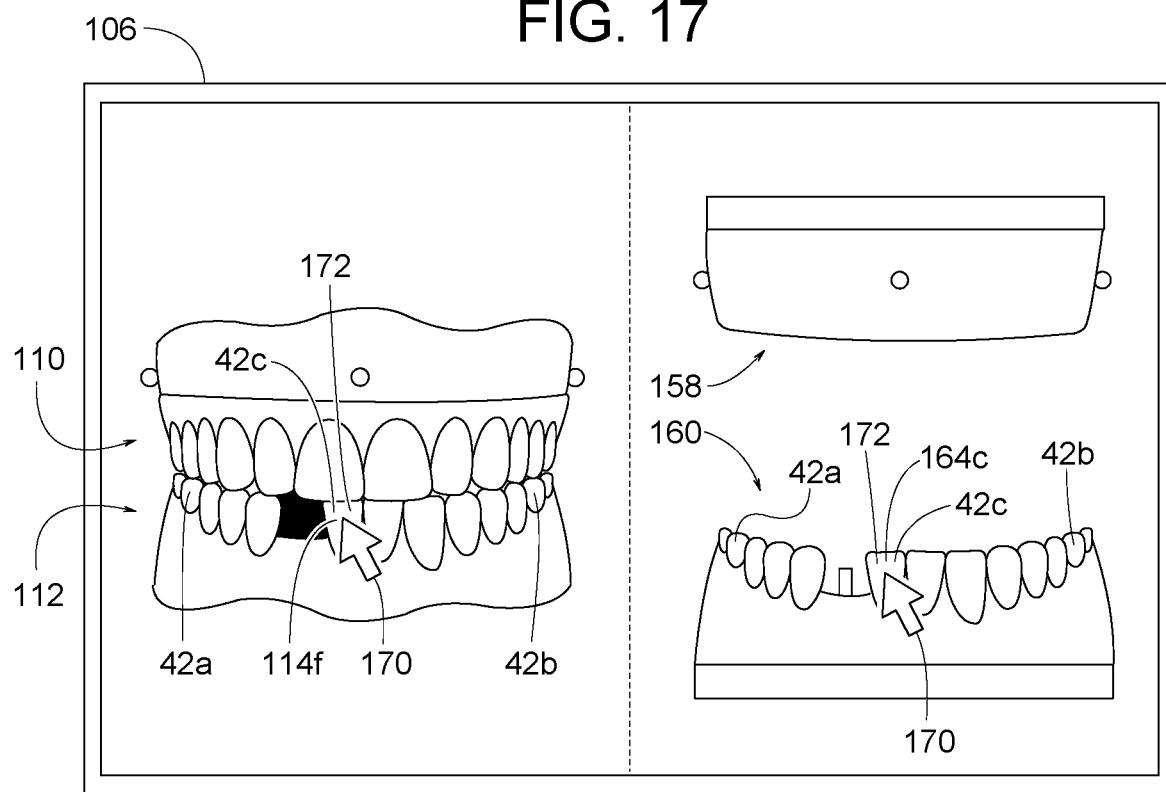
FIG. 17 is front view similar to FIG. 15 but showing a schematic depiction of the dental practitioner mouse-clinking on additional points of the scan results (another illustrative example of a fourth stage or registration stage).
Figure 18:
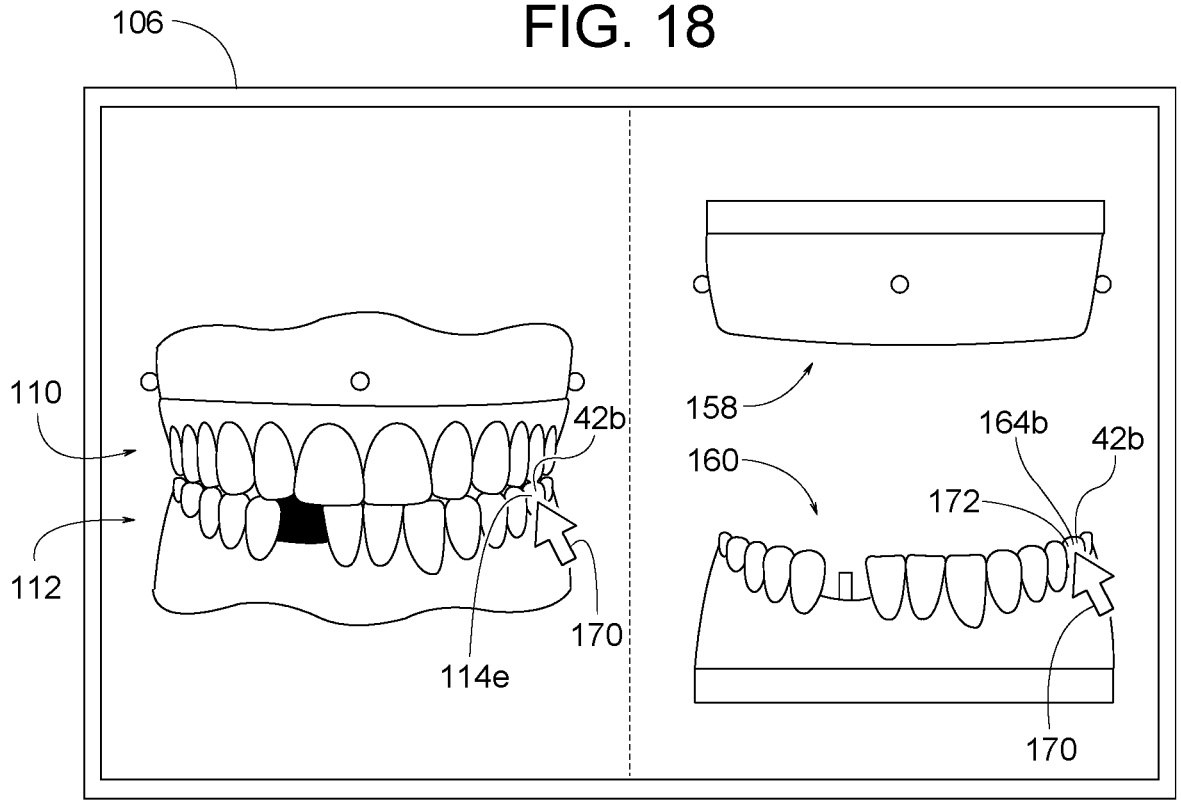
FIG. 18 is front view similar to FIG. 15 but showing a schematic depiction of the dental practitioner mouse-clinking on even more points of the scan results (another illustrative example of a fourth stage or registration stage).

FIGS. 17 and 18 show a similar process being applied to second jaw 12b. FIG. 17 illustrates mouse-clicking 170 on point 114f of first constellation of points 114 and mouse-clicking 170 on point 164c of third constellation of points 164. In response to such mouse-clicking, computer 106 determines that points 114f and 164c represent the same point (feature 42c) on second jaw 12b.

FIG. 18 illustrates mouse-clicking 170 on point 114e of first constellation of points 114 and mouse-clicking 170 on point 164b of third constellation of points 164. In response to such mouse-clicking, computer 106 determines that points 114e and 164b represent the same point (feature 42b) on second jaw 12b. Likewise, similar mouse-clicking on point 114d of first constellation of points 114 and mouse-clicking 170 on point 164a of third constellation of points 164 is interpreted as meaning that points 114d and 164a represent the same point (feature 42a) on second jaw 12b.

The mouse-clicking method, as just described with reference to FIGS. 15-18, ties the second scan representation of the first jaw 158 (e.g., upper jaw 12a) to the first scan representation of the first jaw 110 (e.g., upper jaw 12a). Such mouse-clicking also ties the second scan representation of the second jaw 160 (e.g., lower jaw 12b) to the first scan representation of the second jaw 112 (e.g., lower jaw 12b).

Figure 19:
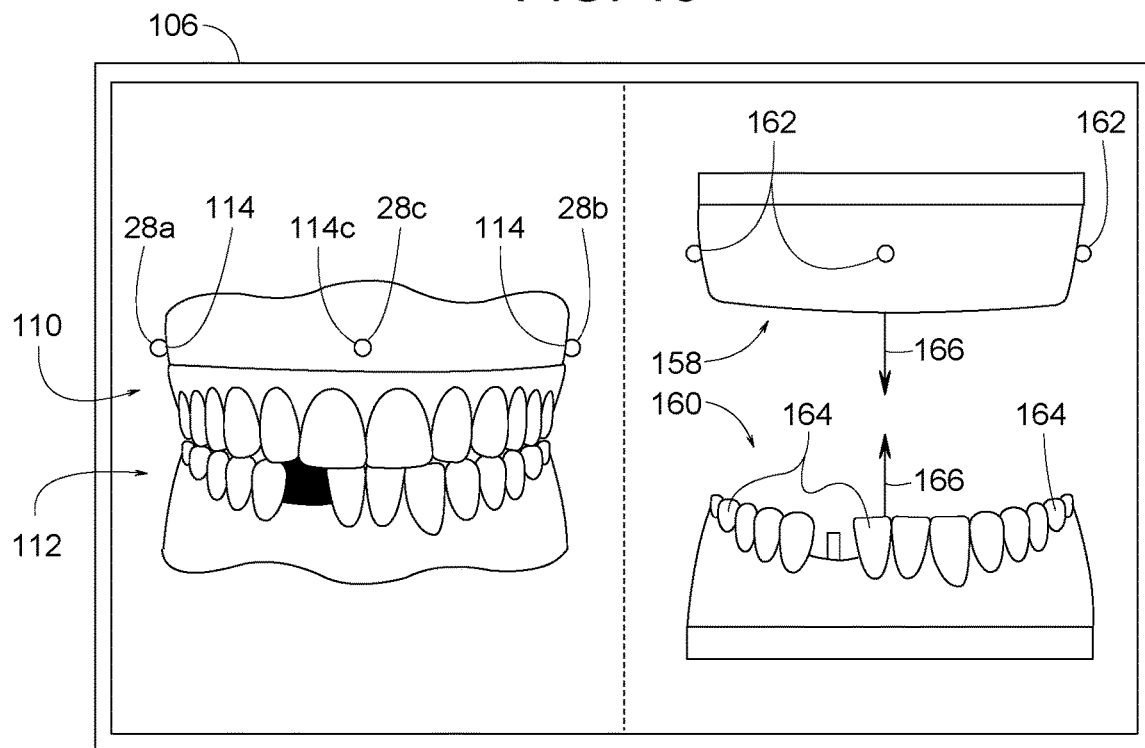
FIG. 19 is a front view similar to FIGS. 15-18 showing upper and lower jaws on the right side of the computer display being shifted to create a digital jaw model having a bite registration that matches that of the upper and lower jaws on the left side (another illustrative example of a fourth stage or registration stage).
Figure 20:
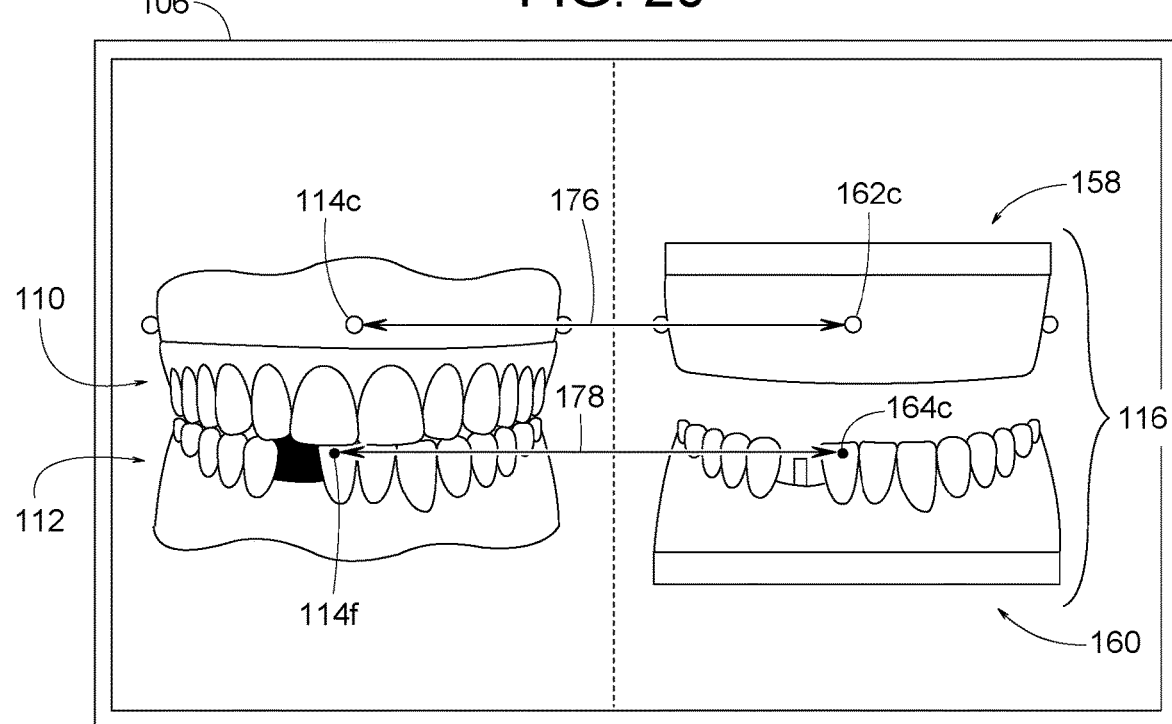
FIG. 20 is a front view similar to FIG. 19 but showing the upper and lower jaws on the right side having been shifted so as to coincide with the positional relationship of the upper and lower jaws on the left side, whereby the jaws on both sides of the display have substantially the same bite registration (another illustrative example of a fourth stage or registration stage).

Next, as shown in FIG. 19, arrows 166 represent shifting the second constellation of points 162 and the third constellation of points 164 relative to each other such that both the second constellation of points 162 and the third constellation of points 164 of the composite constellation of points 174 substantially coincide with the first constellation of points 114. Such shifting creates digital jaw model 116, as shown in FIG. 20, arrow 176 shows how well point 162c of second constellation of points 162 aligns with point 114c of first constellation of points 114. Arrow 178 shows how well point 164c of third constellation of points 164 aligns with point 114f of first constellation of points 114. Consequently, second scan representation of the first jaw 158 and second scan representation of the second jaw 160, of digital jaw model 116, are positioned in proper bite registration in accordance with the bite registration recorded in first scan result 98.

Figure 23:
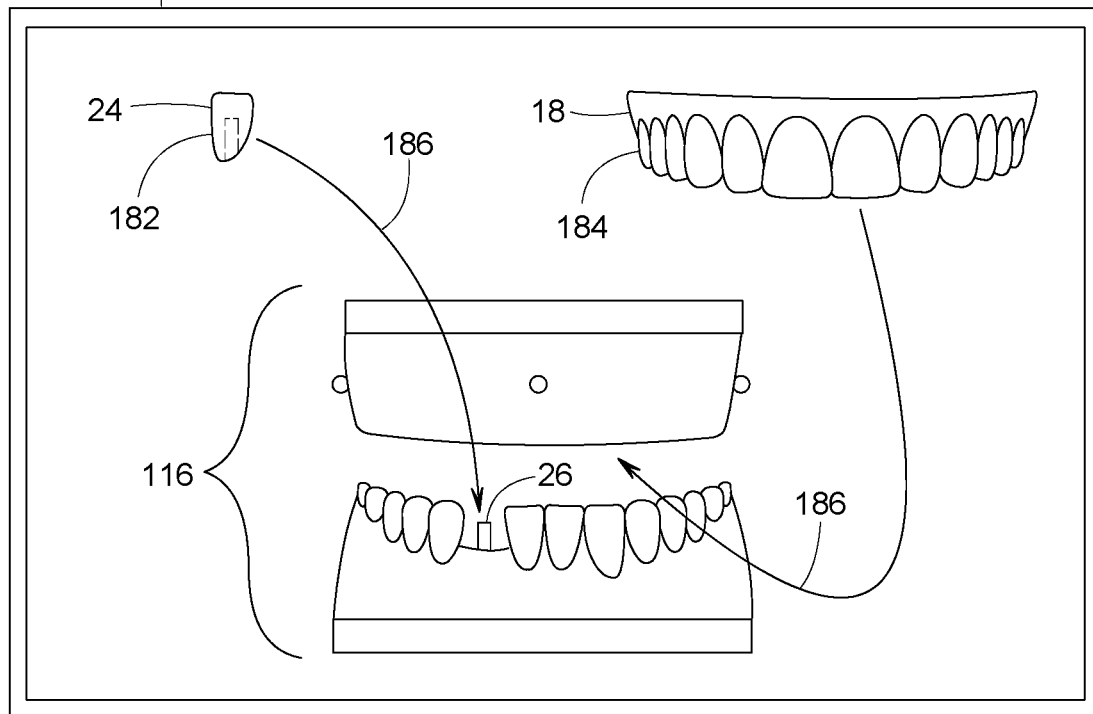
FIG. 23 is a front view of the computer displaying the recently created digital jaw model with virtual teeth and virtual dentures being fitted to the digital jaw model (illustrative example of a fifth stage or treatment stage).
Figure 24:
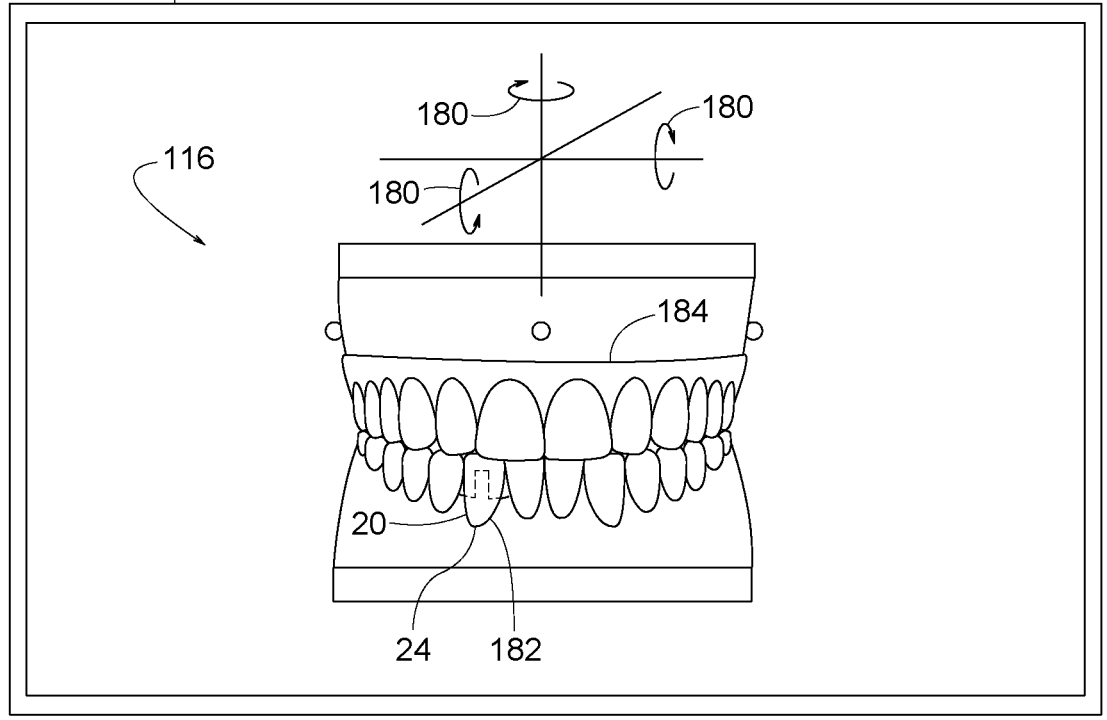
FIG. 24 is a front view similar to FIG. 23 but with the virtual dental appliances fitted in position (illustrative example of a fifth stage or treatment stage).

Once digital jaw model 116 is configured in its proper bite registration, first scan result 98 can be set aside, and dental practitioner 168 can now focus on digital jaw model 116, as shown in FIGS. 23 and 24). To help analyze jaws 12 in the treatment of patient 10, dental practitioner 168 can view digital jaw model 116 from different angles, as known software (e.g., exocad, 3shape, dental wings, Dentsply Sirona, etc.) enables computer 106 to rotate digital jaw model 116 in virtual 3D space. Such 3D rotation is represented by arrows 180 in FIG. 24.

Figure 22:
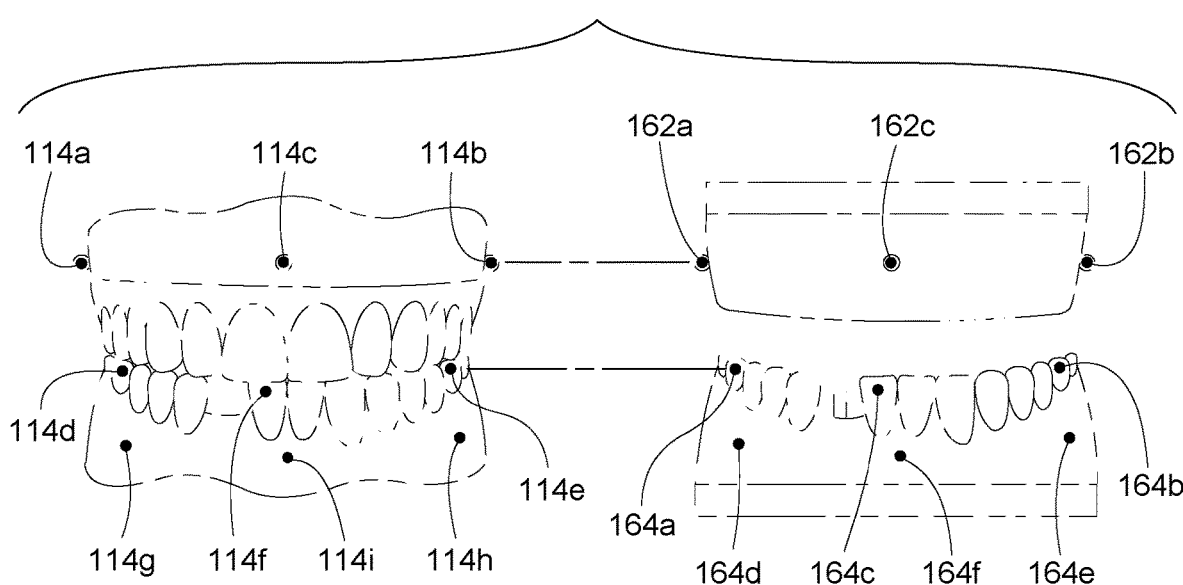
FIG. 22 is a front view similar to FIG. 21 but with some of the constellations of points shifted to another position (another illustrative example of a fourth stage or registration stage).

In the example illustrated in FIGS. 21 and 22, dental practitioner 168 fits a virtual crown 182 (crown 24) and a virtual new set of dentures 184 (dentures 18) to digital jaw model 116. Arrows 186 of FIG. 23 represents adding a virtual dental appliance (e.g., crown 24, dentures 18, etc.) to digital jaw model 116. FIG. 24 shows the expected appearance and fit of crown 24 and dentures 18. If the appearance and fit are acceptable, dental practitioner 168 can 3D print, machine or otherwise create an actual physical crown 24 and dentures 18 that match the proposed virtual ones.

Although fiducial markers 28 can be of any suitable shape and design, FIGS. 25-27 show three examples. In FIG. 25, marker body 36 is generally spherical and is overmolded directly onto an integral extension 188 of screw 38. The slenderness of extension 188 minimizes radiographic interference with marker body 36.

In FIG. 26, marker body 36 is overmolded onto a pin 190 that is sized to fit within a blind hole 192 in screw 38. This allows marker body 36 to be attached to screw 38 for scanning and molding purposes and otherwise removed for the comfort of patient 10. In some examples, pin 190 has a shoulder 194 that ensures repeatable positioning of marker body 36 relative to screw 38. In some examples, pin 190 is tapered for tightly securing pin 190 to screw 38 and for establishing a repeatable stop position of pin 190 within a similarly tapered version of hole 192. Arrows 196 represent selectively attaching marker body 36 to screw 38 and separating marker body 36 from screw 38.

In FIG. 27, a spherical dimple 198 in head 40 of screw 38 provides a suitable surface to which a glue 200 can adhesively bond marker body 36 to head 40. A breakable adhesive bond provides a means for selectively attaching 202 marker body 36 to screw 38 and separating 204 marker body 36 from screw 38.

Here are some additional points worth noting. In FIGS. 14 and 15, marks 206 schematically represent the optional second set 58 of three fiducial markers 28d, 28e and 28f Thus, arrows 146 and 148 of FIG. 14 also represents creating third scan result 126 by not only scanning at least one of the second jaw 12b and physical model 136 of second jaw 12b but by also scanning at least one of second set 58 of three fiducial markers 28d, 28e and 28f attached to second jaw 12b and physical model 136 with an indication (visual image) of the three fiducial markers 28d, 28e and 28f thereon.

In FIG. 10, blocks 208 represent converting first scan result 98 to a digital format substantially equal in format to that of second scan result 124 and third scan result 126. In some examples, the file converting step of block 208 is accomplished through dental treatment planning software executed by computer 106. As mentioned earlier, some examples of such software include exocad, 3shape, dental wings, and Dentsply Sirona. Some example file types include various versions of open mesh data, point cloud data, and DentalCAD HTML scenes. Some specific example file format extensions include .stl, .obj, .ply, .off, .eoff, .xyz, .xyznb.

Arrow 96 of FIG. 10 illustrates creating first scan result 98 by concurrently scanning 100 first jaw 12a and second jaw 12b of patient 10. FIG. 14 illustrates creating second scan result 124 by scanning (arrows 138 and 142) at least one of first jaw 12a and physical model 134 of first jaw 12a, wherein creating first scan result 98 is accomplished using first scanning machine 102, creating second scan result 124 is accomplished using second scanning machine 144, and first scanning machine 102 and second scanning machine 144 are two different machines. FIG. 14 also illustrates creating third scan result 126 by scanning (arrows 146 and 148) at least one of second jaw 12b and physical model 136 of second jaw 12b.

Computer 106 in FIG. 14 illustrates displaying first scan result 98 including first scanned representation of the first jaw 110 (upper jaw 12a) and first scanned representation of the second jaw 112 (lower jaw 12b) in a first positional relationship relative to each other (e.g., jaws 12 in a predetermined proper bite registration). Computer 106 in FIG. 14 illustrates displaying second scan result 124 including second scanned representation of the first jaw 158. Computer 106 in FIG. 14 illustrates displaying third scan result 126 including second scanned representation of the second jaw 160 in a second positional relationship (e.g., jaws 12a and 12b widely spaced apart) relative to second scanned representation of the first jaw 158.

Arrows 166 of FIG. 19 illustrates shifting second scanned representation of the first jaw 158 relative to second scanned representation of the second jaw 160 such that the second positional relationship of second scanned representation of the first jaw 158 relative to the second scanned representation of the second jaw 160 is substantially equal to (as indicated by arrows 176 and 178 of FIG. 20) the first positional relationship of the first scanned representation of the first jaw 110 relative to the first scanned representation of the second jaw 112.

Arrow 118 of FIG. 11 illustrates removing at least one of a tooth and a dental appliance (e.g., dentures 14) from patient 10 after creating first scan result 98 but before creating second scan result 124. Otherwise, failing to remove such items would interfere with second scan result 124 and/or third scan result 126 and thus interfere with planning of the patient's treatment.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

The invention claimed is:

1. A method for analyzing a first jaw and a second jaw of a patient, each of the first jaw and the second jaw includes an alveolar bone, the method involving a pretreatment stage, a CT scan stage, a surface scan stage, a registration stage, and a treatment stage; the method comprising:
   providing three fiducial markers each of which comprise a marker body removably attached to a screw, the screw being tapered, the marker body and the screw each being radiopaque,
   attaching the three fiducial markers to the first jaw by screwing the screw of each of the three fiducial markers directly into the alveolar bone of the first jaw;
   screwing a second set of three fiducial markers directly into the alveolar bone of the second jaw;
   creating a first scan result during the CT scan stage by concurrently scanning the first jaw, the second jaw, the three fiducial markers in the first jaw, and the second set of three fiducial markers in the second jaw;
   creating a second scan result by scanning at least one of the first jaw and a physical model of the first jaw during the surface scan stage, wherein the physical model of the first jaw includes an indication of the three fiducial markers, wherein creating the first scan result is accomplished using a first scanning machine, creating the second scan result is accomplished using a second scanning machine, and the first scanning machine and the second scanning machine are two different kinds of machines;
   creating a third scan result by scanning at least one of the second jaw and a physical model of the second jaw during the surface scan stage, wherein the physical model of the second jaw includes an indication of the second set of three fiducial markers;
   displaying the first scan result including a first scanned representation of the first jaw and a first scanned representation of the second jaw in a first positional relationship relative to each other;
   displaying the second scan result including a second scanned representation of the first jaw with the three fiducial markers;
   displaying the third scan result including a second scanned representation of the second jaw with the second set of three fiducial markers in a second positional relationship relative to the second scanned representation of the first jaw;
   shifting the second scanned representation of the first jaw relative to the second scanned representation of the second jaw such that the second positional relationship of the second scanned representation of the first jaw relative to the second scanned representation of the second jaw is equal to the first positional relationship of the first scanned representation of the first jaw relative to the first scanned representation of the second jaw, wherein shifting the second scanned representation of the first jaw relative to the second scanned representation of the second jaw is performed during the registration stage and done with reference to the three fiducial markers and the second set of three fiducial markers;
   proposing a dental appliance be attached to the first jaw during the treatment stage, wherein the dental appliance is to be spaced apart from the three fiducial markers when the dental appliance is attached to the first jaw; and
   providing the patient with the dental appliance.

2. The method of claim 1, further comprising removing at least one of a tooth and a prior dental appliance from the patient after creating the first scan result but before creating the second scan result.

3. The method of claim 1, wherein the three fiducial markers includes a left fiducial marker, a right fiducial marker and a front fiducial marker, and the method further comprising:
   attaching the left fiducial marker to a left portion of the first jaw;
   attaching the right fiducial marker to a right portion of the first jaw; and
   attaching the front fiducial marker to a front portion of the first jaw.

4. The method of claim 1, wherein the patient includes an oral cavity, and the screw of each of the three fiducial markers points inward toward a central region of the oral cavity when the three fiducial markers are attached to the first jaw.

5. The method of claim 1, wherein each marker body of the three fiducial markers defines a center point, and the three fiducial markers when attached to the first jaw are situated such that:
   a) the center point of the left fiducial marker and the center point of the right fiducial marker define a lateral line intersecting the center point of the left fiducial marker and the center point of the right fiducial marker;
   b) the center point of the front fiducial marker defines a forward line intersecting the center point of the front fiducial marker, intersecting the lateral line, and being perpendicular to the lateral line;
   c) the screw of the left fiducial marker lies within 45 degrees of the lateral line;
   d) the screw of the right fiducial marker lies within 45 degrees of the lateral line; and
   e) the screw of the front fiducial marker lies within 45 degrees of the forward line.

6. The method of claim 1, wherein the first jaw is a maxilla, and the second jaw is a mandible.

7. The method of claim 1, wherein the first jaw is a mandible, and the second jaw is a maxilla.

8. The method of claim 1, further comprising:
   installing a spacer on at least one of the first jaw and the second jaw of the patient to help position the first jaw and the second jaw at a predetermined target bite position relative to each other;
   creating the first scan result by scanning the first jaw, the second jaw, and the three fiducial markers while the first jaw and the second jaw are at the predetermined target bite position relative to each other and while the spacer is still on at least one of the first jaw and the second jaw;
   removing the spacer from the patient;
   creating the second scan result by scanning at least one of the first jaw and the physical model of the first jaw after the spacer has been removed from the patient;
   creating the third scan result by scanning at least one of the second jaw and a physical model of the second jaw after the spacer has been removed from the patient; and
   attaching the dental appliance to at least one of the first jaw and the second jaw to help position the first jaw and the second jaw at the predetermined target bite position relative to each other.

9. The method of claim 8, wherein the spacer is a first denture and the dental appliance is a second denture.

10. The method of claim 1, further comprising converting the first scan result to a digital format equal in format to that of the second scan result and the third scan result.

11. The method of claim 1, further comprising manually identifying a plurality of points that indicate where the three fiducial markers are located on at least one of the first scan result and the second scan result, wherein manually identifying the plurality of points is done by mouse-clicking on the plurality of points.

12. The method of claim 1, wherein the marker body comprises a polymer, and the screw comprises a metal.

13. The method of claim 12, wherein the dental appliance includes a crown to be attached to the implant.

14. The method of claim 1, wherein the dental appliance is an implant to be screwed into the alveolar bone of the patient.

15. The method of claim 1, wherein the dental appliance is a denture to be attached to the first jaw.

16. The method of claim 1, wherein the CT scan stage and the surface scan stage occur after the pretreatment stage, the registration stage occurs after the CT scan stage and the surface scan stage, and the treatment stage occurs after the registration stage.

* * * * *